(12) United States Patent
Husain (10) Patent No.: US 12,247,016 B2
(45) Date of Patent: Mar. 11, 2025

(54) EPOXIDATION PROCESS WITH INCREASED CYCLE WATER ABSORPTION

(71) Applicant: Scientific Design Company, Inc., Little Ferry, NJ (US)

(72) Inventor: Mansoor Husain, North Brunswick, NJ (US)

(73) Assignee: Scientific Design Company, Inc., Little Ferry, NJ (US)

( * ) Notice: Subject to any disclaimer, the term of this patent is extended or adjusted under 35 U.S.C. 154(b) by 412 days.

(21) Appl. No.: 17/692,822

(22) Filed: Mar. 11, 2022

(65) Prior Publication Data

US 2022/0289702 A1    Sep. 15, 2022

Related U.S. Application Data

(60) Provisional application No. 63/159,780, filed on Mar. 11, 2021.

(51) Int. Cl.
*C07D 301/32* (2006.01)

(52) U.S. Cl.
CPC .................................. *C07D 301/32* (2013.01)

(58) Field of Classification Search
CPC .................................................... C07D 301/32
See application file for complete search history.

(56) References Cited

U.S. PATENT DOCUMENTS

| | | |
|---|---|---|
| 3,563,914 A | 2/1971 | Wattimena |
| 3,702,259 A | 11/1972 | Nielsen |
| 4,134,797 A | 1/1979 | Ozero |
| 4,761,394 A | 8/1988 | Lauritzen |
| 4,766,105 A | 8/1988 | Lauritzen |
| 4,908,343 A | 3/1990 | Bhasin |
| 5,011,807 A | 4/1991 | Hayden et al. |
| 5,057,481 A | 10/1991 | Bhasin |
| 5,099,041 A | 3/1992 | Hayden et al. |
| 5,102,848 A | 4/1992 | Soo et al. |
| 5,187,140 A | 2/1993 | Thorsteinson et al. |
| 5,407,888 A | 4/1995 | Herzog et al. |
| 6,452,027 B1 | 9/2002 | Billig et al. |
| 9,067,902 B2 * | 6/2015 | Padia ................... C07D 301/08 |
| 9,096,561 B2 * | 8/2015 | Husain ................ C07D 301/06 |
| 10,351,542 B2 * | 7/2019 | McGovern ................ B01J 8/06 |
| 10,836,738 B2 * | 11/2020 | Chan ................ B01D 53/1487 |
| 10,865,189 B2 * | 12/2020 | McGovern ........... C07D 301/10 |
| 2006/0122449 A1 | 6/2006 | Van Egmond |
| 2007/0037991 A1 | 2/2007 | Rizkalla |
| 2009/0216032 A1 | 8/2009 | Ozero |
| 2010/0063306 A1 | 3/2010 | Osborne et al. |
| 2017/0029352 A1 | 2/2017 | Sookraj et al. |

FOREIGN PATENT DOCUMENTS

| | | |
|---|---|---|
| CN | 203923067 U | 11/2014 |
| WO | 2009105252 A1 | 8/2009 |
| WO | 2019213034 A1 | 11/2019 |

OTHER PUBLICATIONS

International Search Report dated Jun. 10, 2022, received in a corresponding foreign application, 7 pages.
European Search Report dated Aug. 13, 2024, received in a corresponding foreign application, namely European Patent Application No. 22768039.4, 9 pages.

* cited by examiner

*Primary Examiner* — Golam M Shameem
(74) *Attorney, Agent, or Firm* — Scully, Scott, Murphy & Presser, P.C.

(57) ABSTRACT

A process for the preparation of ethylene oxide in which a conventional ethylene oxide process is modified by supplement with a second chiller and a tempered water system.

12 Claims, 3 Drawing Sheets

EPOXIDATION PROCESS WITH INCREASED CYCLE WATER ABSORPTION

CROSS REFERENCE TO RELATED APPLICATION

The present invention claims the benefit of U.S. Provisional Patent Application No. 63/159,780 filed Mar. 11, 2021, the entire content and disclosure of which is incorporated herein by reference.

FIELD OF THE INVENTION

The present invention relates to a method for the oxidation of ethylene into ethylene oxide.

BACKGROUND OF THE INVENTION

Though present in natural settings at minute quantities, ethylene oxide was first synthesized in a laboratory setting in 1859 by French chemist Charles-Adolphe Wurtz using the so-called "chlorohydrin" process. However, the usefulness of ethylene oxide as an industrial chemical was not fully understood in Wurtz's time; and so industrial production of ethylene oxide using the chlorohydrin process did not begin until the eve of the First World War, due at least in part to the rapid increase in demand for ethylene glycol (of which ethylene oxide is an intermediate) as an antifreeze for use in the rapidly growing automobile market. Even then, the chlorohydrin process produced ethylene oxide in relatively small quantities and was highly uneconomical.

The chlorohydrin process was eventually supplanted by another process, the direct catalytic oxidation of ethylene with oxygen, the result of a second breakthrough in ethylene oxide synthesis, discovered in 1931 by another French chemist, Thèodore Lefort. Lefort used a solid silver catalyst with a gas phase feed that included ethylene and utilized air as a source of oxygen.

In the ninety years since the development of the direct oxidation method, the production of ethylene oxide has increased so significantly that today it is one of the largest volume products of the chemicals industry, accounting, by some estimates, for as much as half of the total value of organic chemicals produced by heterogeneous oxidation. Worldwide production in the year 2000 was about 25 billion tons. One of the reasons that ethylene oxide is such a widely produced chemical product is its startling versatility—it is the starting point for innumerable derivatives, including ethylene glycol, ethoxylates, ethanolamines, polyols, and glycol ethers, each of which becomes the raw material for numerous high-value products such as fabrics, moldable plastics, surfactants, detergents, solvents and many others.

Increases in annual production have proceeded in parallel and in fact have been enabled by parallel increases in production plant sizes. While larger plants are more efficient, there are of course diminishing returns to increased plant size. In particular, larger plants require ever larger reactors, which is the major capital cost component for an ethylene oxide/ethylene glycol ("EO/EG") plant. An alternative to larger plants and their larger reactors is to operate at higher work rates and higher percentages of $\Delta$EO. Operating at higher work rates (work rate being the kg of EO produced in reactor per hour per $m^3$ of catalyst) and higher $\Delta$EO (defined as moles of ethylene oxide formed in the reactor per 100 moles of reactor feed) allows more ethylene oxide to be made with the same reactor size and same amount of catalyst. This mode of operation has been further facilitated in recent years by the development of advanced high selectivity catalysts that have been developed that allow high selectivity performance at higher work rates.

Operating this way (at higher work rates/$\Delta$EO) is attractive both for greenfield and revamp projects. For new plant operators, nameplate capacity can be increased without increased capital costs, in particular reactor size, which is the major capital cost component for an EO/EG plant. In a similar way, for revamp projects, which increase the work rate/$\Delta$EO allows for capacity expansion while using essentially the existing equipment, with perhaps only minor additions and replacements. However, this presents difficulties of its own; increasing the work rates/$\Delta$EO means that more ethylene oxide is produced in the reactor and thus the reactor effluent has a higher ethylene oxide concentration. For purposes of both process efficiency and plant safety, it is imperative that the ethylene oxide be rapidly absorbed, forming the rich cycle water in the scrubber after leaving the reactor. This higher amount of ethylene oxide requires, in turn, a higher volume of water in the scrubber bottoms to absorb the ethylene oxide to form the rich cycle water. The larger volume of cycle water not only increases capital costs because of the upsizing of equipment like the ethylene oxide stripping column, exchangers and cycle water pumps; but also the operational costs due to the increased utility requirements to drive the larger pumps and other equipment and supply the additional steam necessary for stripping the larger quantities of ethylene oxide from the larger quantities of rich cycle water. Similarly, increases in the amount of carbon dioxide made under these more exacting process conditions may require a larger carbon dioxide absorber and more utility import for steam-stripping in the carbon dioxide regenerator.

Accordingly, there is a need in the art for efficiently recovering ethylene oxide and separating carbon dioxide from rich cycle water and in an ethylene oxide process operating at higher than typical work rates and ethylene oxide reactor effluent concentrations. By operating more efficiently, higher operating and capital costs can be avoided.

BRIEF SUMMARY OF THE INVENTION

The present invention relates to a process for the preparation of an ethylene oxide stream which includes steps of: providing a reactor effluent containing a concentration of ethylene oxide of from about 1.5 mol % to about 2.5 mol %, preferably about 1.8 mol % to about 2.2 mol %; cooling lean cycle water in a cycle water cooler to a first temperature of about 30° C. to about 50° C.; contacting the reactor effluent with the lean cycle water to prepare a rich cycle water stream and scrubber overheads; separating, in a stripping column, a first stripper column overhead stream from the rich cycle water stream; dividing the scrubber overheads into a treated stream and, optionally, a bypass stream; contacting the treated stream with a carbon dioxide-absorbing solvent to form a remaining gas stream and a rich carbonate solution; separating a regenerator overhead stream from the rich carbonate solution; adding a cycle water chiller and a tempered water system to provide a modified ethylene oxide process; providing to the modified ethylene oxide process a second reactor effluent that contains a concentration of ethylene oxide of from about 2.2 mol % to about 4.0 mol %, preferably about 2.2 mol % to about 3.0 mol %; cooling a second lean cycle water in the cycle water cooler and the cycle water chiller to a second temperature, wherein the second temperature is 4° C. to 15° C. lower than the first temperature; contacting the second reactor effluent with the second lean cycle water to prepare a second rich cycle water stream and second scrubber overheads; separating a second stripping column overhead stream from the second rich cycle water stream; dividing the second scrubber overheads into a second treated stream and, optionally, a second bypass stream; contacting the second treated stream with a second carbon dioxide-absorbing solvent to form a second remaining gas stream and a second carbonate-rich solution; and separating a second regenerator overhead stream from the second rich carbonate solution, wherein the concentration of carbon dioxide in the second regenerator stream is greater than the concentration of carbon dioxide in the regenerator stream and the concentration of the ethylene oxide in the second stripping column overhead stream is greater than the concentration of the ethylene oxide in the first stripping column overhead stream.

BRIEF DESCRIPTION OF THE SEVERAL VIEWS OF THE DRAWINGS

The foregoing summary, as well as the following detailed description of preferred embodiments of the invention, will be better understood when read in conjunction with the appended drawings. For the purpose of illustrating the invention, there is shown in the drawings embodiments which are presently preferred. It should be understood, however, that the invention is not limited to the precise arrangements and instrumentalities shown. In the drawings.

DETAILED DESCRIPTION OF THE INVENTION

All parts, percentages and ratios used herein are expressed by volume unless otherwise specified. All documents cited herein are incorporated by reference.

By "water" it is meant any kind of water suitable for use in chemical and petrochemical processing, including deionized, demineralized, industrial, potable and distilled water.

By the present invention, an improved heat integration scheme has been incorporated into the manufacture of ethylene oxide to improve the efficiency of the process at higher than typical work rates and ethylene oxide reactor effluent concentrations. As a result, the process can be operated at these higher production values without significantly increased operational or capital costs. Specifically, in the present invention, operation at higher work rates and ethylene oxide reactor effluent concentrations results in higher concentrations of ethylene oxide vapor in the stripper overhead (and comparable increases in the carbon dioxide concentration in the regenerator overhead) compared to prior art operation.

The increased amount of available thermal energy due to these higher concentrations of ethylene oxide vapor in the stripper overhead stream and carbon dioxide in the regenerator overhead stream compared to conventional prior art operation makes recirculating streams that provide the hot water driving force for the cycle water chiller. This cycle water chiller in turn reduces the temperature of the lean cycle water supplied to the scrubber to increase the amount of ethylene oxide that is absorbed in the rich cycle water formed in the scrubber.

The use of this invention will now be described in greater detail as a component of an ethylene oxide production process. Specifically the invention will be shown first with respect to a conventional process (FIG. 1) and, second with respect to a conventional process that has been modified in accordance with the present invention (FIG. 2).

Ethylene oxide is produced by continuously contacting an oxygen-containing gas with an olefin, preferably ethylene, in the presence of an ethylene oxide ("epoxidation") catalyst (described in greater detail below). Oxygen may be supplied to the reaction in substantially pure molecular form or in a mixture such as air. By way of example, typical reactant feed mixtures under operating conditions may contain from about 0.5% to about 45%, preferably about 5% to about 30% of ethylene and from about 3% to about 15% oxygen, and from about 0.3% to about 10% carbon dioxide with the balance comprising comparatively inert materials, including such substances as water, inert gases, other hydrocarbons, and the reaction moderators described herein. Non-limiting examples of inert gases include nitrogen, argon, helium and mixtures thereof. Non-limiting examples of the other hydrocarbons include methane, ethane, propane and mixtures thereof. Carbon dioxide and water are byproducts of the epoxidation process as well as common contaminants in the feed gases. Both have adverse effects on the catalyst, so the concentrations of these components are usually kept at a minimum.

Also present in the reaction, as previously mentioned, are one or more reaction moderators, non-limiting examples of which include organic halogen-containing compounds such as $C_1$ to $C_8$ halohydrocarbons; especially preferred are chloride-containing moderators such as methyl chloride, ethyl chloride, ethylene dichloride, vinyl chloride or mixtures thereof. Controlling chloride concentration level is particularly important with rhenium-containing catalysts.

As mentioned above, a usual method for the ethylene epoxidation process comprises the vapor-phase oxidation of ethylene with molecular oxygen, in the presence of an epoxidation catalyst, in a fixed-bed tubular reactor. Conventional, commercial fixed-bed ethylene-oxide reactors are typically in the form of a plurality of parallel elongated tubes (in a suitable shell) approximately 0.7 to 2.7 inches O.D. and 0.5 to 2.5 inches I.D. and 15-53 feet long, each filled and packed with catalyst. The reaction feed mixture (described above) is introduced into these tubes, and the resulting reactor effluent gas contains ethylene oxide, un-used reactants, and byproducts.

As mentioned above, in the present invention the reactor is run at higher work rates and ΔEO than conventionally employed. The work rate is the production rate and is represented herein by the units $kg/m^3/h$. The ΔEO is defined as the moles of EO formed in the reactor per 100 moles of reactor feed and essentially represents the concentration of ethylene oxide in the reactor effluent, since the concentration of ethylene oxide in reactor feed must be maintained at very close to zero, indeed typically only a few ppm.

In ethylene oxide process, the typical work rate is between 130 and 200 $kg/m^3/h$, while the ΔEO is between 1.5% and 2.5%. By contrast in the present invention, the work rate (EO production rate) is greater than 200 $kg/m^3/h$, preferably between about 220 and about 300 $kg/m^3/h$. The ΔEO is also comparatively higher than in conventional operation. The feed composition of the reactor inlet after the completion of start-up and during normal operation typically comprises (by volume %): 10-70% methane, 1-40% ethylene, 3-12% $O_2$; 0.3% to 20%, preferably 0.3 to 5%, more preferably 0.3 to 1% of $CO_2$; 0-3% ethane, an amount of one or more chloride moderators, which are described herein; and the balance of the feed being comprised of argon, methane, nitrogen or mixtures thereof.

Typical operating conditions for the reactor are temperatures (as measured in the shell side coolant of the reactor) in the range from about 180° C. to about 330° C., and preferably from about 200° C. to about 325° C., and more preferably from about 225° C. to about 280° C. The operating pressure may vary from about 1 atmosphere to about 30 atmospheres, depending on the mass velocity and productivity desired. Higher pressures may be employed within the scope of the invention. Residence times in commercial-scale reactors are generally on the order of about 2 to about 20 seconds.

Figure 1:
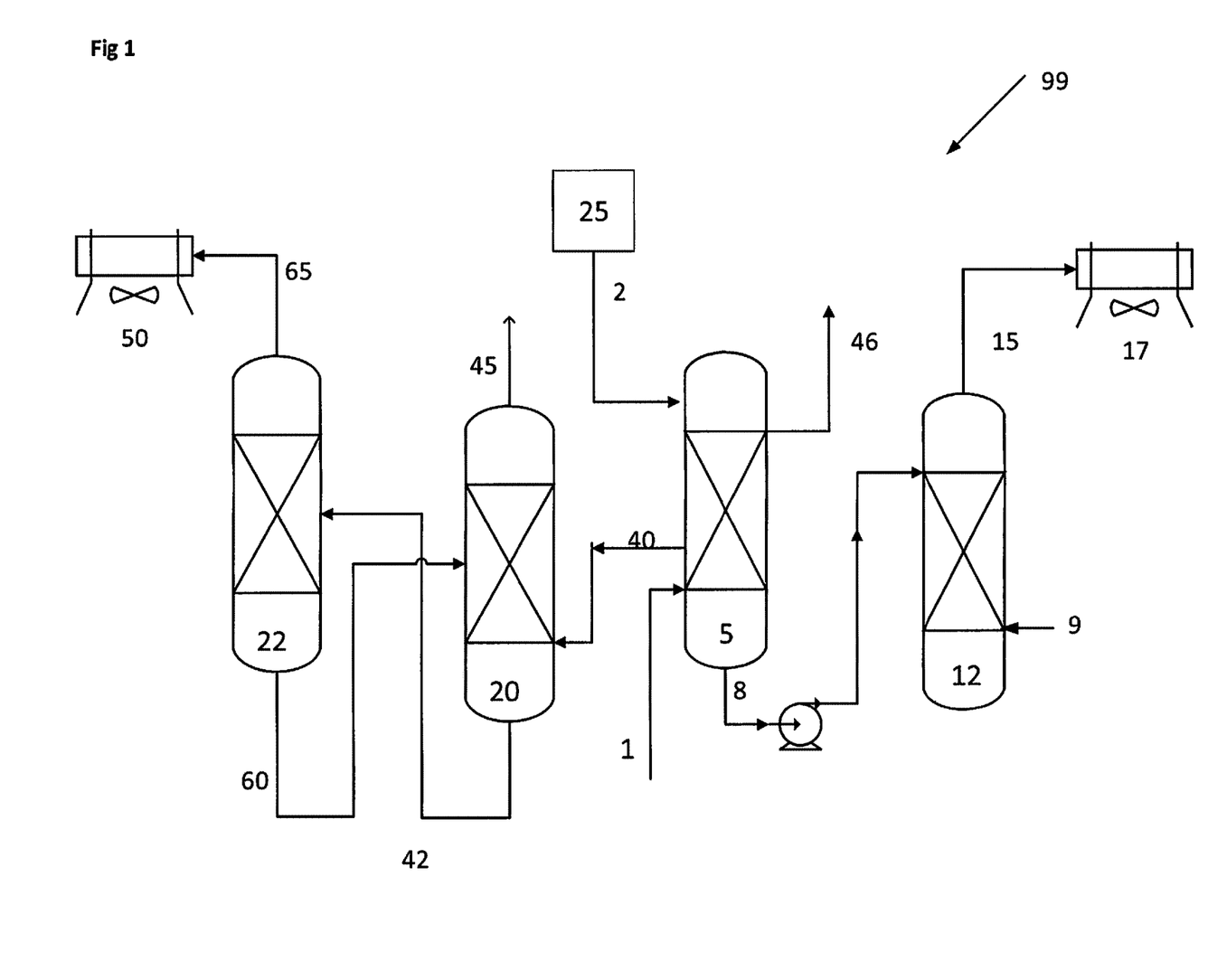
FIG. 1 is a schematic flow sheet showing a conventional, prior art process for making ethylene oxide.
Figure 2:
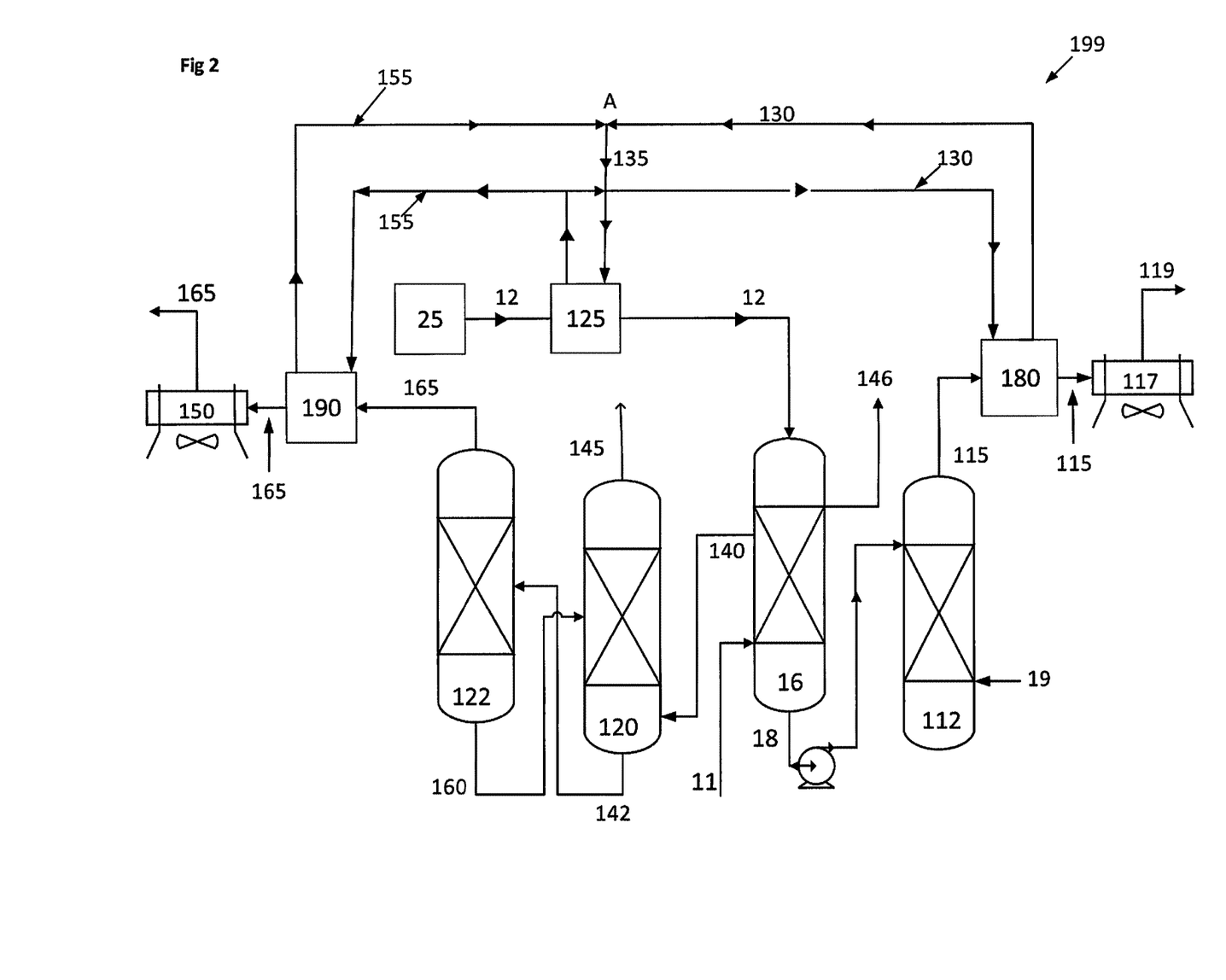
FIG. 2 is a schematic flow sheet showing a process for making ethylene oxide according to the present invention.

FIG. 1 shows a conventional, prior art ethylene oxide production process 99. The reactor effluent 1 flows to the scrubber 5. The reactor effluent 1 contains a concentration of ethylene oxide of from about 1.5 mol % to about 2.5 mol %, preferably about 1.8 mol % to about 2.2 mol %. In addition to ethylene oxide, the reactor effluent 1 may also contain inert and unreacted gases supplied as components of the reactor feed such as argon, methane, ethylene and oxygen; reaction byproducts, in particular, carbon dioxide, but also ppm levels of formaldehyde, formic acid, acetic acid, and product isomers such as acetaldehyde; and additionally sulfur and other impurities, again typically at ppm or ppb levels. The lean cycle water 2 is cooled in a cooler 25 before being sent to the scrubber 5. In the scrubber 5, the reactor effluent is contacted with the recirculated lean cycle water 2 to scrub the ethylene oxide from the reactor effluent thereby forming rich cycle water. Besides ethylene oxide, the rich cycle water may also contain inerts and unreacted gases supplied as components of the reactor feed such as methane, ethylene, argon, and oxygen; as well as carbon dioxide, the main byproduct of the epoxidation of ethylene; and in addition to ppm levels of impurities and isomers such as formaldehyde, formic acid, acetic acid and acetaldehyde.

The temperature of the lean cycle water 2 is regulated in order to maximize the amount of ethylene oxide absorbed into in the rich cycle water and minimize the presence of other components in the rich cycle water. Typically, the lean cycle water 2 is cooled in the cooler 25 prior to entering the scrubber 5 to increase the amount of ethylene oxide that is absorbed into the rich cycle water. The temperature of the lean cycle water 2 is in the range of about 30° C. to about 50° C. The pressure in the scrubber 5 is maintained within a sufficient range so that the "light" gases that have a volatility greater than that of ethylene oxide are directed by pressure differential to rise upwardly to the top of the scrubber 5 forming the scrubber overheads, while the ethylene oxide solute stays largely solubilized within the rich cycle water stream in the liquid bottoms (some light gases may be metastably solubilized in the rich cycle water but they will quickly flash out into the scrubber overhead leaving only traces of light gases still dissolved in the rich cycle water). These more volatile "light" gases that compose the scrubber overheads include the aforementioned inert, unreacted or byproducts found in the reactor effluent, including of course carbon dioxide. Accordingly, in order to ensure the balance between flashing the more volatile light solutes while maintaining high solubility of ethylene oxide the rich cycle water, the pressure in the scrubber 5 is maintained in a range about 10 atm to about 25 atm. Nonetheless, traces of ethylene oxide may also vaporize with the more volatile light gases in the rich cycle water stream. These small amounts of ethylene oxide that effervesce out of the rich cycle water (preferably the scrubber overheads contain less than 10 ppm of ethylene oxide), and rise into the scrubber overhead with the light gas solute vapor are recovered subsequently at a later point that is not relevant to this invention. The resulting first rich cycle water produced in the first scrubber 5 contains from about 1.5 wt % to about 2.5 wt % ethylene oxide.

The first rich cycle water in the scrubber 5 bottoms flows as stream 8 and is pumped to the top portion of the stripping column 12 and as the first rich cycle water moves downward in the stripping column 12, separation by steam-stripping of the rich cycle water takes place with upwardly-moving steam contacting the rich cycle water and separating an ethylene oxide rich steam from the rich cycle water to form a gaseous stripping column overhead. The ethylene oxide rich-gaseous stripping column overhead comprises ethylene oxide, water vapor, carbon dioxide and additional impurities in trace amounts. Ethylene oxide is removed as a result of this stripping action. The stripping column 12 is operated at a pressure of about 1 atm to about 3 atm, while the bottoms temperature of the stripping column 12 is about 100° C. to about 125° C. and the bottoms contains a lean cycle water solution having had all or most of its ethylene oxide separated away so that it contains less than 50 molar ppm ethylene oxide. Steam 9 is provided to the stripping column 12 in order to effect the separation by steam stripping. This steam is supplied from either: (1) steam generated elsewhere in the ethylene oxide production facility, e.g., in the reactor steam drum or (2) medium- or high-pressure steam supplied externally/OSBL; or a combination of these two sources. The separation efficiency of EO from the rich cycle water may also be enhanced by use of a steam ejector system well-known to those skilled in the art.

The stripping column overhead 15 contains a significant amount of excess heat because of the steam 9 that is directly provided for the steam-stripping that takes place in the stripping column 12 in order to separate the ethylene oxide from the rich cycle water. The temperature of the stripping column overhead 15 is then reduced in a cooler 17 to partially condense the water and ethylene oxide thereby forming a liquid-vapor mixture (not shown). The cooler 17 may be an air cooler such as, for example, a fin fan cooler (illustrated in FIGS. 1 and 2) and sent for further processing. From the cooler 17, the resulting liquid-vapor mixture is directed to an ethylene oxide reabsorber (not shown), in which the uncondensed ethylene oxide vapor is reabsorbed in water. A predominance of the carbon dioxide and gaseous inerts which remain unabsorbed are readily separated as gaseous overhead stream from this reabsorption step. An aqueous solution is thus obtained which contains the reabsorbed ethylene oxide and aldehyde impurities, such as formaldehyde and acetaldehyde, as well as dissolved carbon dioxide and other gaseous impurities, and which ethylene oxide must be either further treated to either provide purified ethylene oxide or reacted in various proportions with water to make an ethylene glycol homolog.

Having previously described the scrubber bottoms at the other end the scrubber overhead treated stream 40 travels to the carbon dioxide absorber 20. The treated stream 40 contains valuable hydrocarbons and therefore in order increase the economic efficiency of the ethylene oxide process it is imperative that these be recovered and recycled back to the reactor inlet feed. In particular, the treated stream 40 may contain between about 20 mol % to about 50 mol % ethylene and about 5 mol % to about 60 mol % methane. In addition to trace amounts of other light gases, the scrubber overhead also, of course, contains carbon dioxide. As mentioned above carbon dioxide is a byproduct of the epoxidation process and it has an adverse effect on the performance of high selectivity catalysts. This carbon dioxide must be removed from the treated stream 40 so that the ethylene and methane in treated stream 40 can be recycled back to the reactor.

Carbon dioxide removal occurs in the carbon dioxide absorber 20, where the carbon dioxide solubilized in the treated stream 40 is removed. The resulting remaining gas stream 45, which contains ethylene and methane can then be recycled back to the reactor inlet feed allowing for the recovering and reused of these gases. At least a portion and up to 100% of the scrubber overheads is sent as the treated stream 40 to the carbon dioxide absorber 20, This is illustrated in FIG. 1, in which a treated stream 40 from the scrubber overheads is sent to the carbon dioxide absorber 20 for carbon dioxide removal while a bypass stream 46 is preferably recycled back to the reactor inlet without treatment in the carbon dioxide absorber to remove carbon dioxide.

Nonetheless, a sufficiently high amount of the overhead gases in the scrubbing column 5 must be sent as the treated stream 40 to the carbon dioxide absorber 20 in order to reduce the amount of carbon dioxide to produce a remaining gas stream 45 with a relatively low level of carbon dioxide. Removing as much of the carbon dioxide as possible allows the recycling back to the reactor of the hydrocarbon feedstock, such as ethylene and methane, in the remaining gas stream 45. So for example, when about 20% of the scrubber overheads is fed to the carbon dioxide absorber 5 the amount of carbon dioxide present in the remaining gas stream 45 will be of such a quantity that the inlet reactor feed will be about 7 vol. % carbon dioxide. However, for lower carbon dioxide concentrations, for example to maintain 1 vol. % carbon dioxide in the inlet reactor feed, substantially all of the scrubber overheads must be fed to the carbon dioxide absorber 20.

As mentioned above, the bypass stream 46 is 'preferably' recycled back to the reactor inlet because while it would be possible to simply vent the untreated bypass stream to the atmosphere, this would almost never be done intentionally given the loss of valuable hydrocarbons in the bypass stream and the requirement for extensive emissions treatment prior to venting. Nonetheless, it is a possible under the operational constraints of emergencies that the bypass stream could be partially vented.

Any process or technique known to the person of ordinary skill for removing carbon dioxide from a gaseous feed is acceptable in the present invention. Preferably, a carbon dioxide-containing stream is contacted with a carbon dioxide-absorbing solvent so that carbon dioxide is readily solubilized and absorbed into solvent. Specifically, as shown in FIG. 1, the treated stream 40 from the carbon dioxide-containing scrubber overhead is contacted with a carbon dioxide-absorbing solvent in the carbon dioxide absorber 20 to form a carbon dioxide-rich solvent phase and a carbon dioxide-depleted gas phase. Preferably the carbon dioxide-absorbing solvent is potassium carbonate; the carbon dioxide reacts with the potassium carbonate to form potassium bicarbonate thereby removing the carbon dioxide. In a particularly preferred embodiment the steps in the carbon dioxide absorber are carried out by reactive distillation.

At the bottom of the carbon dioxide absorber the carbon dioxide-rich solvent phase exits the carbon dioxide absorber 20 as the rich carbonate solution 42 and flows by pressure differential to the regenerator 22, which operates at near atmospheric pressure. In the regenerator 22, the carbon dioxide is separated from the carbon dioxide-rich solvent using steam to yield a gaseous carbon dioxide-rich regenerator overhead stream 65 and a lean solvent 60, the lean solvent 60 then being returned to the carbon dioxide absorber 20 ready to absorb additional carbon dioxide.

The regenerator overhead 65 contains a significant amount of excess heat because of the aforementioned steam-stripping that takes place in the regenerator in order to separate the carbon dioxide from the rich carbonate solution. As was the case with the stripping column overhead 15, the temperature of the gaseous carbon dioxide-rich regenerator overhead 65 is reduced in a cooler 50. For the choice of the appropriate cooler, see the discussion above with respect to the type of cooler 17 used to cool the first stripping column overhead 15.

Figure 3:
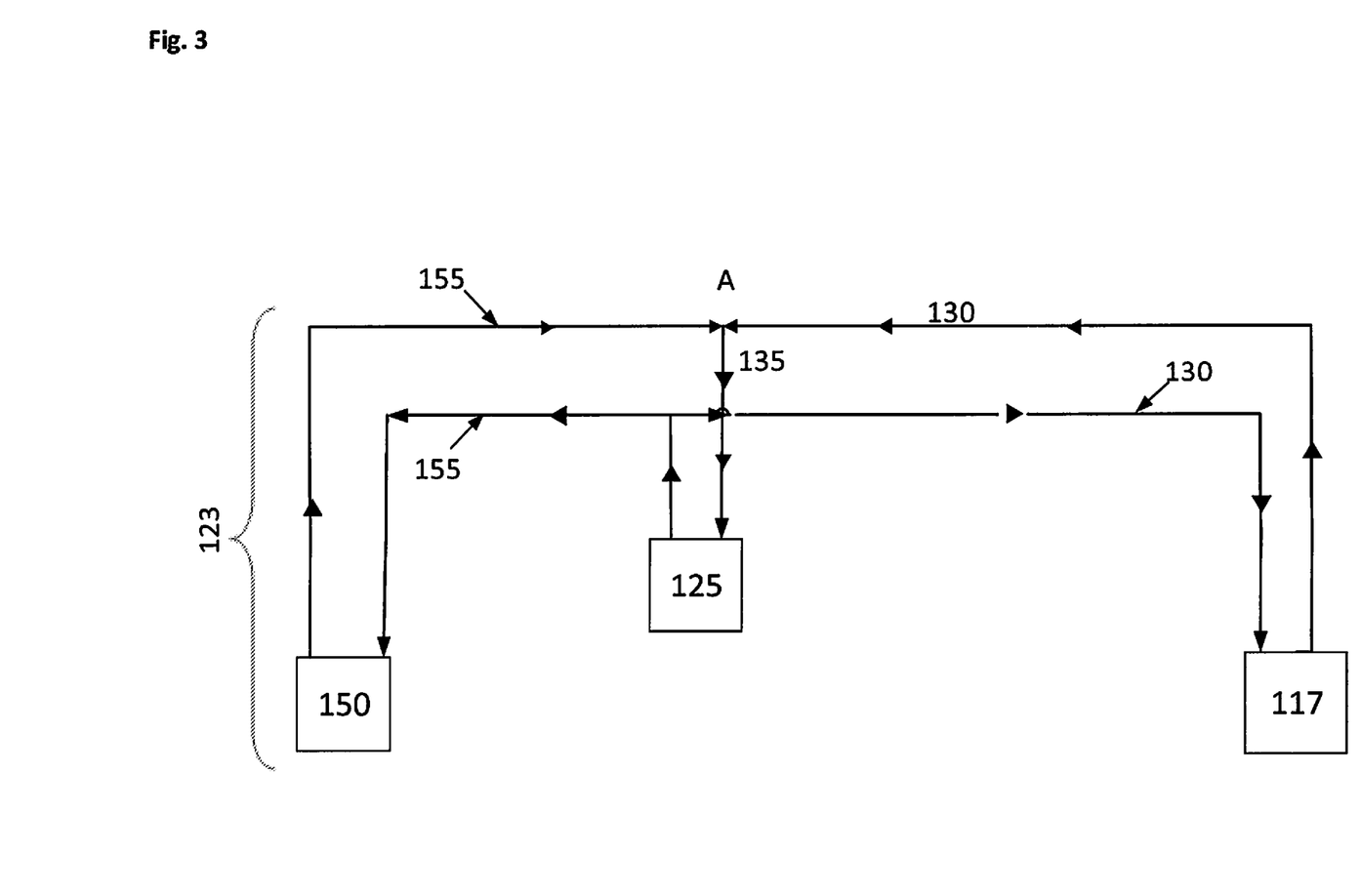
FIG. 3 is a schematic flow sheet showing the tempered water system according to the present invention.

Now referring to FIG. 2 and FIG. 3, which show a modified ("inventive") ethylene oxide process 199 in accordance with the present invention in which the tempered water system 125 is added to the ethylene oxide process 99. As mentioned above, in this modified ethylene oxide process 199, the reactor is operated at higher work rates and ethylene oxide reactor effluent concentrations. Accordingly, the second reactor effluent 11 contains a higher concentration of ethylene oxide than the reactor effluent 1 in ethylene oxide process 99. Specifically, the second reactor effluent 11 contains a concentration of ethylene oxide of from about 2.2% mol % to about 4.0 mol %, preferably about 2.2 mol % to about 3.0 mol %.

As can be seen in FIG. 2, in the modified ethylene oxide process 199, the cooler 25 of the ethylene oxide process 99 is supplemented with a tempered water system 123 as shown in FIG. 3 thereby greatly improving the efficiency and economics of the process. Referring to FIGS. 2 and 3, as presently illustrated, the tempered water system 123 has ends on the second stripping column overhead 115 and the regenerator overhead 165 which provide indirect heating to the first tempered water loop 130, and a second tempered water loop 155, respectively. The loops 130 and 155 of the tempered water system combine at point A to form the combined heated stream 135 which feeds and powers the cycle water chiller 125. Having passed through the cooler 25, the second lean cycle water 12 then passes through the cycle water chiller 125 and this second lean cycle water 12 then enters the second scrubber 16. Thus, the second lean cycle water 12 is cooled by being passed through both the cooler 25 and the cycle water chiller 125 to temperatures lower than in conventional ethylene oxide processes. Specifically, the stream 12 is 4° C. to 15° C. cooler than the temperature of stream 2. As mentioned above, the chiller—second lean cycle water 12 passes from the cycle water chiller 125 to the second absorber 15 where it is ready to absorb even higher concentrations of ethylene oxide from the second reactor effluent 11 than is absorbed by the first scrubber 5.

It should be noted that the additional power required to run the tempered water system 123 is more than offset by the power saving due to the lower condensation requirements of the regenerator overhead 165 and stripper overhead 115 in coolers 117 and 150, respectively.

The cycle water chiller 125 is a hot water-driven absorption chiller. In the present invention, the hot water-driven absorption chiller is preferred to other coolers such as electrically-operated or steam-operated since the latter two refrigeration technologies require outside utility supply. By contrast, the hot water-driven absorption unit of the present invention makes use of the waste heat from the regenerator and stripper overhead streams to heat the aforementioned tempered water streams and the combined heated stream 135 for providing the hot water driving force for the hot water driven absorption chiller. Any suitable hot water driven absorption refrigeration unit or technology known to those of ordinary skill can be used in the present invention.

Again, referring to the modified ethylene oxide process 199 in FIG. 2, the second reactor effluent 11 flows to the second scrubber 16. As in the conventional or prior art ethylene oxide process, the second lean cycle water 12 flows through and is cooled in the cooler 25 and then additionally, the second lean cycle water 12 is cooled in the cycle water chiller 125 and then recirculated to the second scrubber 16. In the second scrubber 16, the reactor effluent 11 is contacted with recirculated second lean cycle water 12 to form the second rich cycle water in the second scrubber 16 bottoms in which nearly all of the ethylene oxide from the second reactor effluent 11 is absorbed. In the present invention, the second lean cycle water stream 12 is cooled in the cooler 25 and cycle water chiller 125 well below the temperature level of the comparable second lean cycle water 2 in order to increase the amount of ethylene oxide that can be absorbed in the second lean cycle water 12 in the second scrubber 16; in this way, the same volume of lean cycle water as was used in ethylene oxide process 99 can absorb the larger quantity of ethylene oxide that is produced in the ethylene oxide process 199 by running the reactor at a higher work rate. Preferably the temperature of the second lean cycle water 12 as supplied to and upon entering the scrubber 15 is between about 20° C. to about 40° C., preferably about 25° C. to about 35° C. At these lower temperatures, the amount of ethylene oxide absorbed in the second rich cycle water is much higher, from about 2.5 mol % to about 6 mol %—this is as much as twice the level of ethylene oxide found in the rich cycle water stream 8 of the ethylene oxide process 99. However, additional energy is required to power the second chiller 125 to provide this additional cooling of the second lean cycle water 12 to increase the amount of ethylene oxide absorbed. In the present invention, this additional cooling is provided by the tempered water system 123 as mentioned above and discussed in further detail below.

The second rich cycle water in the second scrubber 16 bottoms flows as stream 18 and enters into the top portion of the second stripping column 112 and as the second rich cycle water moves downward in the column, separation by steam-stripping of the product solution takes place as described above with respect to the second stripping column 112 in the conventional ethylene oxide process 99. A second steam stream 19 provides a first amount of steam to the stripping column 112 for steam-stripping, however, in the inventive process 199 the second amount of steam provided in the second steam stream 19 is less than the first amount of steam because the second rich cycle water is more enriched than the first rich cycle water and therefore requires less steam for stripping. Similarly, compared to the second stripping column overhead 15 in the separation section of the conventional ethylene oxide process 99, the second stripping column overhead 115 of the present invention is more enriched in ethylene oxide, and less enriched in water vapor-steam; preferably the second stripping column overhead 115 in the inventive modified ethylene oxide process 199 contains about 60 wt % to about 75 wt % ethylene oxide with the balance vapor-steam.

With respect to the operational temperatures and pressures of the second stripping column 112, the second stripping column 112 is operated at a pressure of about 1 atm to about 3 atm, while the bottoms temperature of the stripping column 112 is about 100° C. to about 125° C. The second stripping column overhead stream 115 has a temperature of about 90° C. to about 115° C. As mentioned above with respect to the conventional ethylene oxide process 99, in the inventive process 199 it is necessary to cool and condense the second stripping column overhead 115. In the conventional ethylene oxide process 99 described above this is done in an air cooler with the excess heat being treated as waste and released into the atmosphere. This imposes an economic and process efficiency penalty not only because of the wasted heat but because of energy to power the equipment to dissipate it, like electrically operated fin fan coolers. This penalty gets worse in circumstances like those of the present invention, where the high concentration of ethylene oxide increases the amount of heat that must be removed.

However, in the inventive ethylene oxide process 199 rather than simply treat this as waste heat, the excess thermal energy provided by the higher ethylene oxide content of the second stripping column overhead stream 115 makes the stream highly useful for heat integration. Specifically, in the present invention this stream 115 helps provide the hot water driving force for the second chiller 125 via the tempered water system 123. Specifically, the second stripping column overhead steam 115 passes through the first heat exchanger 180 with first tempered water loop 130 coming from the second chiller 125 on the other side of the exchanger. The first tempered loop 130 is thus heated by indirect heat exchange with the second stripping column overhead stream 115 in the first heat exchanger 180 so that the temperature of the first tempered water loop 130 is raised from a temperature of about 65° C. to about 75° C. prior to entering the first heating exchanger 180 to a temperature of about 75° C. to about 85° C. for the heated first tempered water loop 130 after exiting after the heat exchanger 180.

After exchanging heat in the exchanger 180 with the first tempered water loop 130 the second stripping column overhead 115 may require still additional cooling which takes place in cooler 117. For the choice of the appropriate type or design of the cooler see the discussion above with respect to the type of cooler used to cool the first stripping column overhead 15. As above with respect to the stripping column 12 and the cooler 17, the second stripping column overhead 115 is partially condensed in cooler 117 with the water and ethylene oxide thereby forming a second liquid-vapor mixture 119. The second liquid vapor mixture is then directed to a second ethylene oxide reabsorber (not shown) which is operated as the reabsorber described above.

The treated stream 140 from the scrubber overheads travel to the carbon dioxide absorber 120. As described above the scrubber overhead treated stream 140 contain valuable hydrocarbons that must be recycled back to the reactor inlet feed. (The bypass stream 146 is also illustrated). The carbon dioxide absorber 120 is operated as described above with respect to the comparable carbon dioxide absorber 20 in the conventional ethylene oxide process 99. However, removal of carbon dioxide is particularly important in the inventive ethylene oxide process 199 because higher work rates mean more carbon dioxide is produced and thus, carbon dioxide concentrations are considerably higher in the scrubber overhead treated stream 140 than in the corresponding scrubber overheads of the conventional ethylene oxide process 99.

Rather than being sent to the second carbon dioxide absorber 120, an optional second bypass stream 146 may be recycled back to the reactor inlet stream without treatment in the carbon dioxide absorber to remove carbon dioxide. As mentioned above, in the present invention carbon dioxide concentrations in the reactor outlet and hence in the rich cycle water and second scrubber overhead treated stream 140 are higher and so generally a high proportion of the second scrubber overhead stream 140 are treated in the carbon dioxide absorber 120. Specifically, the volume ratio of stream 140: stream 146 is about 0.2:10 to about 0.2:1.

The second scrubber overhead treated stream 140 is contacted with a second carbon dioxide-absorbing solvent in the second carbon dioxide absorber 120. Preferably, a second carbon dioxide-containing stream is contacted with a carbon dioxide absorbing solvent so that carbon dioxide is readily solubilized and absorbed into solvent. Specifically, the second carbon dioxide-containing second scrubber overhead treated stream 140 is contacted with a carbon dioxide-absorbing solvent in the second carbon dioxide absorber 120 to form a carbon dioxide-rich solvent phase and a carbon dioxide-depleted gas phase. Thus, from the second treated stream 140 two additional streams are created: (1) a second carbonate-rich solution 142 which is sent to the second regenerator 122 from the bottom of the carbon dioxide absorber 120; and (2) in the overhead second remaining gas stream 145 reduced in carbon dioxide concentration—specifically having a carbon dioxide content of between about 0.3 mol % and 3 mol %.

Preferably the carbon dioxide-absorbing solvent is potassium carbonate; carbon dioxide reacts with the potassium carbonate to form potassium bicarbonate thereby removing the carbon dioxide. In a particularly preferred embodiment, the steps in the carbon dioxide absorber are carried out by reactive distillation.

Although not shown in the figure, the second remaining gas steam 145 is preferably subjected to additional process steps before being fed back to the inlet reactor feed. Specifically, the second remaining gas stream 145 from the second carbon dioxide absorber 120 is preferably subjected to a cooling step by direct contact with cooled wash water reducing the water content of the second remaining gas stream 145 while also scrubbing it of contained carbonate, which would deleteriously affect the ethylene oxide catalyst were it to be returned to the ethylene oxide reactor through the reactor inlet feed. High concentrations of water may also hurt catalyst performance and by cooling the water content of the second remaining gas stream 145 is reduced to a level that does not inhibit catalyst activity. See, e.g., U.S. Pat. No. 6,452,027.

The second regenerator 122 is constructed and operated as described above with respect to the regenerator 22 in the conventional ethylene oxide process 99 above. Carbon dioxide is separated from the carbon dioxide-rich solvent stream 142 using steam stripping to yield a second lean solvent 160 recycled through the bottoms back to the second carbon dioxide absorber 120 and a carbon dioxide-rich gaseous second regenerator overhead stream 165 having a temperature of about 90° C. to about 120° C. It is preferable that special column internals (not shown) be positioned that at the top of the regenerator to minimize carbonate solution entrainment into the vapor and reduce the carbonate that is carried away in the second regenerator overhead 165.

Because of the higher carbon dioxide content in the second regenerator overhead stream 165, the excess thermal energy in this stream is highly useful for heat integration. (This is analogous to the higher ethylene oxide content in the stripper overhead stream 115, as discussed above). Specifically, the second regenerator overhead stream 165 has a carbon dioxide concentration of between 5% and 10% higher than the carbon dioxide concentration of stream 65. The second regenerator overhead 165 passes through the second heat exchanger 190 and exchanges heat with the second tempered loop 155 coming from the chiller on the other side of the exchanger 190. The second tempered loop 155 is thus heated by indirect heat exchange with the second regenerator overhead 165 so that after passing through the exchanger 190 the temperature of the heated second tempered water loop 155 is raised from a temperature of about 65° C. to about 75° C. prior to entering heat exchanger 190 to a temperature of about 70° C. to about 90° C. after exiting.

After exchanging heat in the exchanger 190 with the second tempered loop 155, the second regenerator overhead 165 may require still additional cooling which takes place in cooler 150. For the choice of the appropriate type or design of the cooler see the discussion above with respect to the type of cooler used to cool the first stripping column overhead.

Although not shown in the figure, the carbon dioxide absorber 20 may be directly affixed to the scrubber 5. In this embodiment the absorber 20 is directly and permanently affixed to the top surface of the scrubber 5, by for example, welding. However, this is not a necessary part of the invention and they may be prepared as entirely separate components/columns.

Under the circumstances of process streams, specifically the stripping column overhead having a higher than conventional ethylene oxide concentration, operators will continue to maintain appropriate safety standards that are always observed when producing, handling or storing ethylene oxide. As always, measures must be taken to prevent reactions or events that could result in ignition, combustion, deflagration, detonation or explosion of any gas stream, but especially those containing higher than typical concentrations of ethylene oxide. Accordingly, to prevent such events relief valves may be used to relieve or reduce undesirable pressure built-up in the process, reaction, or separation systems or elsewhere in the ethylene oxide plan both upstream and downstream of what is illustrated. In the present invention such risk is extremely small given that the ethylene oxide-enriched reactor effluent is quickly absorbed into an aqueous stream. Additionally, the separation in the stripper is very effective so that nearly all of the ethylene oxide in the rich cycle water that enters the stripper is successfully separated and recovered from the rich cycle water and leaves the stripper as vapor overhead while only a small portion leaves the stripper as liquid bottoms.

In the present invention, the conventional ethylene oxide process 99 is modified to the ethylene oxide process 199 by incorporating the chiller 125 and supplementing with the tempered water system 123. It is an advantage of the present invention in order to modify the ethylene oxide process 99 to the ethylene oxide process 199 requires the process be only briefly taken off-line. No equipment modifications are necessary and it is easy to erect new equipment during normal plant operation followed by a brief process interruption while the new equipment is incorporated into the process. This also provides extra flexibility in cases where documentation fails to accurately describe the as-built conditions of the plant and further modifications need to be made. In such cases, the plant can continue to operate normally while such changes are made.

Accordingly, in one embodiment the conventional ethylene oxide process is not permanently replaced by the modified ethylene oxide process operation. Rather, in this embodiment, the present invention provides sufficient flexibility to alternate between the conventional ethylene oxide process (with the lean cycle water is cooled in the cooler 25) and the modified ethylene oxide process operation (with the lean cycle water is cooled in the chiller 125 and its accompanying tempered water system 123) when the plant operator wishes to do so in the event that technical or economic circumstances make one process particularly more desirable than the other.

Silver-Based Epoxidation Catalyst

The silver-based epoxidation catalyst includes a support, and at least a catalytically effective amount of silver or a silver-containing compound; also optionally present is a promoting amount of rhenium or a rhenium-containing compound; also optionally present is a promoting amount of one or more alkali metals or alkali-metal-containing compounds. The support employed in this invention may be selected from a large number of solid, refractory supports that may be porous and may provide the preferred pore structure. Alumina is well known to be useful as a catalyst support for the epoxidation of an olefin and is the preferred support.

Regardless of the character of the support used, it is usually shaped into particles, chunks, pieces, pellets, rings, spheres, wagon wheels, cross-partitioned hollow cylinders, and the like, of a size suitable for employment in a fixed-bed epoxidation reactor. The support particles will preferably have equivalent diameters in the range from about 3 mm to about 12 mm, and more preferably in the range from about 5 mm to about 10 mm. (Equivalent diameter is the diameter of a sphere having the same external surface (i.e., neglecting surface within the pores of the particle) to volume ratio as the support particles being employed.) Suitable supports are available from Saint-Gobain Norpro Co., Sud Chemie AG, Noritake Co., CeramTec AG, and Industrie Bitossi S.p.A. Without being limited to the specific compositions and formulations contained therein, further information on support compositions and methods for making supports may be found in U.S. Patent Publication No. 2007/0037991.

In order to produce a catalyst for the oxidation of an olefin to an olefin oxide, a support having the above characteristics is then provided with a catalytically effective amount of silver on its surface. In one embodiment, the catalytic effective amount of silver is from 10% by weight to 45% by weight. The catalyst is prepared by impregnating the support with a silver compound, complex or salt dissolved in a suitable solvent sufficient to cause deposition of a silver-precursor compound onto the support. Preferably, an aqueous silver solution is used.

A promoting amount of a rhenium component, which may be a rhenium-containing compound or a rhenium-containing complex may also be deposited on the support, either prior to, coincidentally with, or subsequent to the deposition of the silver. The rhenium promoter may be present in an amount from about 0.001 wt. % to about 1 wt. %, preferably from about 0.005 wt. % to about 0.5 wt. %, and more preferably from about 0.01 wt. % to about 0.1 wt. % based on the weight of the total catalyst including the support, expressed as the rhenium metal.

Other components which may also be deposited on the support either prior to, coincidentally with, or subsequent to the deposition of the silver and rhenium are promoting amounts of an alkali metal or mixtures of two or more alkali metals, as well as optional promoting amounts of a Group IIA alkaline earth metal component or mixtures of two or more Group IIA alkaline earth metal components, and/or a transition metal component or mixtures of two or more transition metal components, all of which may be in the form of metal ions, metal compounds, metal complexes and/or metal salts dissolved in an appropriate solvent. The support may be impregnated at the same time or in separate steps with the various catalyst promoters. The particular combination of support, silver, alkali metal promoter(s), rhenium component, and optional additional promoter(s) of the instant invention will provide an improvement in one or more catalytic properties over the same combination of silver and support and none, or only one of the promoters.

As used herein the term "promoting amount" of a certain component of the catalyst refers to an amount of that component that works effectively to improve the catalytic performance of the catalyst when compared to a catalyst that does not contain that component. The exact concentrations employed, of course, will depend on, among other factors, the desired silver content, the nature of the support, the viscosity of the liquid, and solubility of the particular compound used to deliver the promoter into the impregnating solution. Examples of catalytic properties include, inter alia, operability (resistance to runaway), selectivity, activity, conversion, stability and yield. It is understood by one skilled in the art that one or more of the individual catalytic properties may be enhanced by the "promoting amount" while other catalytic properties may or may not be enhanced or may even be diminished.

Suitable alkali metal promoters may be selected from lithium, sodium, potassium, rubidium, cesium or combinations thereof, with cesium being preferred, and combinations of cesium with other alkali metals being especially preferred. The amount of alkali metal deposited or present on the support is to be a promoting amount. Preferably, the amount ranges from about 10 ppm to about 3000 ppm, more preferably from about 15 ppm to about 2000 ppm, and even more preferably from about 20 ppm to about 1500 ppm, and as especially preferred from about 50 ppm to about 1000 ppm by weight of the total catalyst, measured as the metal.

Suitable alkaline earth metal promoters comprise elements from Group IIA of the Periodic Table of the Elements, which may be beryllium, magnesium, calcium, strontium, and barium or combinations thereof. Suitable transition metal promoters may comprise elements from Groups IVA, VA, VIA, VIIA and VIIIA of the Periodic Table of the Elements, and combinations thereof.

The amount of alkaline earth metal promoter(s) and/or transition metal promoter(s) deposited on the support is a promoting amount. The transition metal promoter may typically be present in an amount from about 0.1 micromoles per gram to about 10 micromoles per gram, preferably from about 0.2 micromoles per gram to about 5 micromoles per gram.

The silver solution used to impregnate the support may also comprise an optional solvent or a complexing/solubilizing agent such as are known in the art. A wide variety of solvents or complexing/solubilizing agents may be employed to solubilize silver to the desired concentration in the impregnating medium. Useful complexing/solubilizing agents include amines, ammonia, oxalic acid, lactic acid and combinations thereof. Amines include an alkylene diamine having from 1 to 5 carbon atoms. In one preferred embodiment, the solution comprises an aqueous solution of silver oxalate and ethylene diamine. The complexing/solubilizing agent may be present in the impregnating solution in an amount from about 0.1 to about 5.0 moles per mole of silver, preferably from about 0.2 to about 4.0 moles, and more preferably from about 0.3 to about 3.0 moles for each mole of silver.

When a solvent is used, it may be an organic solvent or water, and may be polar or substantially or totally non-polar. In general, the solvent should have sufficient solvating power to solubilize the solution components. At the same time, it is preferred that the solvent be chosen to avoid having an undue influence on or interaction with the solvated promoters. Organic-based solvents which have 1 to about 8 carbon atoms per molecule are preferred. Mixtures of several organic solvents or mixtures of organic solvent(s) with water may be used, provided that such mixed solvents function as desired herein.

The concentration of silver in the impregnating solution is typically in the range from about 0.1% by weight up to the maximum solubility afforded by the particular solvent/solubilizing agent combination employed. It is generally very suitable to employ solutions containing from 0.5% to about 45% by weight of silver, with concentrations from 5 to 35% by weight of silver being preferred.

Impregnation of the selected support is achieved using any of the conventional methods; for example, excess solution impregnation, incipient wetness impregnation, spray coating, etc. Typically, the support material is placed in contact with the silver-containing solution until a sufficient amount of the solution is absorbed by the support. Preferably the quantity of the silver-containing solution used to impregnate the porous support is no more than is necessary to fill the pores of the support. A single impregnation or a series of impregnations, with or without intermediate drying, may be used, depending, in part, on the concentration of the silver component in the solution. Impregnation procedures are described, for example, in U.S. Pat. Nos. 4,761,394, 4,766,105, 4,908,343, 5,057,481, 5,187,140, 5,102,848, 5,011,807, 5,099,041 and 5,407,888. Known prior procedures of pre-deposition, co-deposition and post-deposition of various the promoters can be employed.

After impregnation of the support with the silver-containing compound, i.e., a silver precursor, a rhenium component, an alkali metal component, and the optional other promoters, the impregnated support is calcined for a time sufficient to convert the silver containing compound to an active silver species and to remove the volatile components from the impregnated support to result in a catalyst precursor. The calcination may be accomplished by heating the impregnated support, preferably at a gradual rate, to a temperature in the range from about 200° C. to about 600° C. at a pressure in the range from about 0.5 to about 35 bar. In general, the higher the temperature, the shorter the required heating period. A wide range of heating periods have been suggested in the art; e.g., U.S. Pat. No. 3,563,914 discloses heating for less than 300 seconds, and U.S. Pat. No. 3,702,259 discloses heating from 2 to 8 hours at a temperature of from 100° C. to 375° C., usually for duration of from about 0.5 to about 8 hours. However, it is only important that the heating time be correlated with the temperature such that substantially all of the contained silver is converted to the active silver species. Continuous or step-wise heating may be used for this purpose.

During calcination, the impregnated support may be exposed to a gas atmosphere comprising an inert gas or a mixture of an inert gas with from about 10 ppm to 21% by volume of an oxygen-containing oxidizing component. For purposes of this invention, an inert gas is defined as a gas that does not substantially react with the catalyst or catalyst precursor under the conditions chosen for the calcination. Further information on catalyst manufacture may be found in the aforementioned U.S. Patent Publication No. 2007/0037991.

For purposes of illustration only, the following are conditions that are often used in current commercial ethylene oxide reactor units: a gas hourly space velocity (GHSV) of 1500-10,000 h$^{-1}$, a reactor inlet pressure of 1 MPa to 3 MPa, a coolant temperature of 180-315° C., an oxygen conversion level of 10-60%, and an EO production rate (work rate) of 100-350 kg EO/m$^3$ catalyst/hr and a change in ethylene oxide concentration, ΔEO, of from about 1.5% to about 4.5%. The feed composition in the reactor inlet after the completion of start-up and during normal operation typically comprises (by volume %) 1-40% ethylene, 3-12% $O_2$; 0.2% to 10%, preferably 0.2% to 6%, more preferably 0.2% to 5% of $CO_2$; 0-5% ethane, an amount of one or more chloride moderators, which are described herein; and the balance of the feed being comprised of argon, methane, nitrogen or mixtures thereof.

EXAMPLES

The invention will now be described in more detail with respect to the following non-limiting examples.

An ethylene oxide process prepared according to a conventional, prior art ethylene oxide process 99 and according to the present invention 199 are shown in FIGS. 1 and 2, respectively, and were simulated using PRO/II software. The conventional ethylene oxide process 99 utilizes a cooler 25 that is independent of the regenerator overhead 65 and the stripping column overhead 15. By contrast, the ethylene oxide process prepared according to the present invention 199 includes in addition to cooler 25 additionally a tempered water system 123 with chiller 125. The chiller 125 is powered by tempered water loops 130, 155, which are, in turn, powered by heat exchange with the regenerator overhead 165 and the stripper overhead 115 in exchangers 190, 180 respectively. The compositions of the streams were as follows:

TABLE 1

| | $H_2O$ (wt %) | EO (wt %) |
|---|---|---|
| Stripping Column overhead (#15) (Conventional EO Process #99) | 36 | 62 |
| 2nd Stripping Column overhead (#115) (Inventive EO Process #199) | 34 | 65 |

As described above, in the present invention the stripper column overhead contains higher concentrations of ethylene oxide vapor compared to prior art operation (compare stream #115 to stream #15).

Furthermore, the benefits of the present invention are represented in Table 2, which compares the heat load necessary for steam-stripping separation in the first and second stripping columns as calculated by the aforementioned simulation. As can be seen, the amount of steam in the second steam stream (present invention/inventive EO process #199) is considerably reduced compared to the first steam stream (conventional EO process #99). In fact this reduction is over 12%.

TABLE 2

| | kg/h |
|---|---|
| First steam stream (#9) to EO Stripping Column (#12) in Conventional EO Process (#99) | 77,500 |
| Second steam stream (#19) to Second EO Stripping Column (#112) in modified or inventive EO process (#199) | 68,900 |

I claim:

1. A process for the preparation of ethylene oxide stream comprising:
   (a) providing a reactor effluent containing a concentration of ethylene oxide of from about 1.5 mol % to about 2.5 mol %;
   (b) cooling lean cycle water in a cooler to a first temperature of about 30° C. to about 50° C.;
   (c) contacting the reactor effluent with the lean cycle water to prepare a rich cycle water stream and scrubber overheads;
   (d) separating, in a stripping column, a first stripping overhead stream from the rich cycle water stream;
   (e) dividing the scrubber overheads into at least a treated stream;
   (f) contacting the treated stream with a carbon dioxide-absorbing solvent to form a remaining gas stream and a rich carbonate solution;
   (g) separating a regenerator overhead stream from the rich carbonate solution;
   (h) adding a cycle water chiller and a tempered water system to provide a modified ethylene oxide process;
   (i) providing to the modified ethylene oxide process a second reactor effluent that contains a concentration of ethylene oxide of from about 2.2 mol % to about 4.0 mol %;
   (j) cooling a second lean cycle water in the cycle water cooler and the chiller to a second temperature, wherein the second temperature is 4° C. to 15° C. lower than the first temperature;
   (k) contacting the second reactor effluent with the second lean cycle water to prepare a second rich cycle water stream and second scrubber overheads;
   (l) separating a second stripping column overhead stream from the second rich cycle water stream;
   (m) dividing the second scrubber overheads into at least a second treated stream;
   (n) contacting the second treated stream with a second carbon dioxide-absorbing solvent to form a second remaining gas stream and a second carbonate-rich solution; and
   (o) separating a second regenerator overhead stream from the second rich carbonate solution,
   wherein the concentration of carbon dioxide in the second regenerator stream is greater than the concentration of carbon dioxide in the regenerator stream and the concentration of the ethylene oxide in the second stripping column overhead stream is greater than the concentration of the ethylene oxide in the stripping column overhead stream.

2. The process of claim 1, wherein the tempered water system further includes a first and second tempered water loop and the process further comprises the steps of exchanging heat between the second stripping column overhead stream and the first tempered water loop and between the second rich carbon dioxide stream and the second tempered water loop to yield a heated first tempered water loop and a heated second tempered water loop.

3. The process of claim 1, wherein the second chiller is the hot water-driven absorption chiller type.

4. The process of claim 1, wherein the tempered water system further includes a first and second tempered water loops, wherein the first and second tempered water loops are combined to form a combined heated stream and directing the combined heated stream to the second chiller to provide hot water driving force to the second chiller; the second chiller being a hot water-driven absorption chiller.

5. The process of claim 2, wherein a temperature of the heated second tempered water loop is from about 70° C. to about 90° C.

6. The process of claim 1, further comprising the steps of partially condensing the second stripping column overhead stream into a second liquid-vapor mixture and directing the second liquid-vapor mixture to a second reabsorber.

7. The process of claim 1, wherein a temperature of the second regenerator overhead is from about 90° C. to about 120° C.

8. The process of claim 1, wherein the second remaining gas stream has a carbon dioxide concentration of about 0.3 mol % and 3 mol %.

9. The process of claim 1, wherein a first amount of steam is provided to the first stripping column and a second amount of steam is provided to the second stripping column and the first amount of steam is less than the second amount of steam.

10. The process of claim 1, wherein the concentration of ethylene oxide in the reactor effluent is from about 1.8 mol % to 2.2 mol %.

11. The process of claim 1, wherein the concentration of ethylene oxide in the second reactor effluent is from about 2.2 mol % to 3.0 mol %.

12. A process for the preparation of ethylene oxide stream comprising:
   (a) providing a reactor effluent containing a concentration of ethylene oxide of from about 1.5 mol % to about 2.5 mol;
   (b) cooling lean cycle water in a cooler to a first temperature of about 30° C. to about 50° C.;
   (c) contacting the reactor effluent with the lean cycle water to prepare a rich cycle water stream and scrubber overheads;
   (d) separating, in a stripping column, a first stripping overhead stream from the rich cycle water stream;
   (e) dividing the scrubber overheads into a treated stream and a bypass stream;
   (f) contacting the treated stream with a carbon dioxide-absorbing solvent to form a remaining gas stream and a rich carbonate solution;
   (g) separating a regenerator overhead stream from the rich carbonate solution;
   (h) adding a cycle water chiller and a tempered water system to provide a modified ethylene oxide process;
   (i) providing to the modified ethylene oxide process a second reactor effluent that contains a concentration of ethylene oxide of from about 2.2 mol % to about 4.0 mol %;
   (j) cooling a second lean cycle water in the cycle water cooler and the chiller to a second temperature, wherein the second temperature is 4° C. to 15° C. lower than the first temperature;
   (k) contacting the second reactor effluent with the second lean cycle water to prepare a second rich cycle water stream and second scrubber overheads;
   (l) separating a second stripping column overhead stream from the second rich cycle water stream;
   (m) dividing the second scrubber overheads into a second treated stream and a second bypass stream;
   (n) contacting the second treated stream with a second carbon dioxide-absorbing solvent to form a second remaining gas stream and a second carbonate-rich solution; and
   (o) separating a second regenerator overhead stream from the second rich carbonate solution, wherein the concentration of carbon dioxide in the second regenerator stream is greater than the concentration of carbon dioxide in the regenerator stream and the concentration of the ethylene oxide in the second stripping column overhead stream is greater than the concentration of the ethylene oxide in the stripping column overhead stream.

\* \* \* \* \*